US012805762B2

(12) United States Patent
Verschueren et al.

(10) Patent No.: US 12,805,762 B2
(45) Date of Patent: Nov. 24, 2026

(54) SENSOR DEVICE AND A METHOD FOR MANUFACTURING A SENSOR DEVICE

(71) Applicant: Stichting IMEC Nederland, Eindhoven (NL)

(72) Inventors: Alwin Rogier Martijn Verschueren, 's-Hertogenbosch (NL); Mark Fichman, Eindhoven (NL)

(73) Assignee: Stichting IMEC Nederland, Eindhoven (NL)

(*) Notice: Subject to any disclaimer, the term of this patent is extended or adjusted under 35 U.S.C. 154(b) by 355 days.

(21) Appl. No.: 18/388,287

(22) Filed: Nov. 9, 2023

(65) Prior Publication Data

US 2024/0156372 A1 May 16, 2024

(30) Foreign Application Priority Data

Nov. 11, 2022 (EP) .................................... 22206887

(51) Int. Cl.
*A61B 5/145* (2006.01)
*A61B 5/1459* (2006.01)
*A61B 5/1473* (2006.01)

(52) U.S. Cl.
CPC ........ *A61B 5/14528* (2013.01); *A61B 5/1459* (2013.01); *A61B 5/1473* (2013.01); *A61B 2562/12* (2013.01)

(58) Field of Classification Search
CPC . A61B 5/14528; A61B 5/1459; A61B 5/1473; A61B 2562/12; A61B 5/0031;
(Continued)

(56) References Cited

U.S. PATENT DOCUMENTS 5,640,954 A * 6/1997 Pfeiffer .............. A61B 5/14865 604/890.1
6,330,464 B1 12/2001 Colvin, Jr. et al.
(Continued)

FOREIGN PATENT DOCUMENTS

EP 1184351 B1 11/2003
EP 3385762 A1 10/2018

OTHER PUBLICATIONS

Baj-Rossi et al: "In-Vivo Validation of Fully Implantable Multi-Panel Devices for Remote Monitoring of Metabolism", IEEE Transactions on Biomedical Circuits and Systems, vol. 10, No. 5, pp. 955-962, 2016.

(Continued)

*Primary Examiner* — Etsub D Berhanu
*Assistant Examiner* — Om Patel
(74) *Attorney, Agent, or Firm* — MOSER TABOADA

(57) ABSTRACT

A sensor device for sensing a property of a biological material comprises: a biocompatible enclosure comprising a barrier having a first and a second surface; a sensor receptor element arranged at the first surface; a substrate arranged at the second surface carrying an electronic or photonic circuitry comprising a sensor transducer element for reading out signals from the sensor receptor element; and wherein at least one compartment of the biocompatible enclosure is configured to control transport of the biological material into the compartment or is configured to form a hermetical seal around the substrate.

18 Claims, 5 Drawing Sheets

(58) Field of Classification Search
CPC ... A61B 5/145; A61B 5/14503; A61B 5/1455; A61B 5/1486; A61B 5/14865; A61B 5/686
See application file for complete search history.

(56) References Cited

U.S. PATENT DOCUMENTS

| | | | | |
|---|---|---|---|---|
| 7,479,108 | B2 | 1/2009 | Rini et al. | |
| 7,898,074 | B2 | 3/2011 | Eckhardt et al. | |
| 8,578,795 | B2 | 11/2013 | Crivelli | |
| 9,259,591 | B2 | 2/2016 | Brown et al. | |
| 9,636,780 | B2 | 5/2017 | Maattanen | |
| 9,717,413 | B2 | 8/2017 | Colvin et al. | |
| 10,638,962 | B2 | 5/2020 | Lucisano et al. | |
| 2011/0201312 | A1* | 8/2011 | Peterson .......... | G01N 33/54393 455/466 |
| 2022/0089474 | A1 | 3/2022 | Onezawa et al. | |
| 2022/0183558 | A1 | 6/2022 | Mikhail | |
| 2022/0241897 | A1 | 8/2022 | Thomas et al. | |

OTHER PUBLICATIONS

Clement: “Brain-Computer Interface Technologies”, Chapter 4, The Human Body: A Special Environment, pp. 97-200, Springer Nature Switzerland AG 2019.
Fernandes et al: “Design and Evaluation of a Lactate Microbiosensor: Toward Multianalyte Monitoring of Neurometabolic Markers In Vivo in the Brain”, Molecules, 27, 514, pp. 1-17, 2022.
Naresh et al: “A Review on Biosensors and Recent Development of Nanostructured Material-Enabled Biosensors”, Sensors, 21, 1109, pp. 1-35, 2021.
Zhang et al: “Electrochemical Array Microsystem with Integrated Potentiostat”, IEEE Sensors, pp. 385-388, 2005.
Du et al: “Silica hermetic packages based on laser patterning and localized fusion bonding”, 2018 IEEE Micro Electro Mechanical Systems (MEMS), Belfast, UK, pp. 551-554, 2018.
Hulanicki et al: “Chemical Sensors Definitions and Classification”, Pure and Applied Chemistry, vol. 63, No. 9, pp. 1247-1250, 1991.
European Extended Search Report for Application No. 23207749.5 dated Mar. 21, 2024, 10 pages.

* cited by examiner

SENSOR DEVICE AND A METHOD FOR MANUFACTURING A SENSOR DEVICE

CROSS-REFERENCE TO RELATED APPLICATIONS

The present application claims the benefit of and priority to EP Patent Application Serial No. 22206887.6, filed Nov. 11, 2022, the entire contents of which is incorporated herein by reference.

TECHNICAL FIELD

The present description relates to a sensor device for sensing a property of a biological material. The present description further relates to a method for manufacturing such sensor device.

BACKGROUND

A sensor device for sensing a property of a biological material may be used in various applications, such as for monitoring a health condition of a human being or an animal. Sensor devices are increasingly used as implantable sensor devices, wherein the sensor device is implanted in the human being or the animal.

In many applications, it is desired for the sensor device to be used over a long period of time. The sensor device can thus be used for repeatedly performing measurements, such as measuring concentrations of specific analytes in blood or other biological fluids, in order to provide monitoring of the analyte. A major challenge for achieving a long operational lifetime of the sensor device is to ensure that the sensor device maintains functionality when being exposed to an active immune system. When the sensor device is implanted, the sensor device will be exposed to the active immune system. However, the sensor device may also be exposed to the active immune system, when performing measurements outside a body, such as when the sensor device is configured to perform measurements on blood during dialysis.

There is a need for improvement of sensor devices in order to ensure a long operational lifetime of the sensor devices.

SUMMARY

An objective of the present description is to provide a sensor device which is adapted for sensing a property of a biological material while reducing a risk that the sensor device is damaged by the biological material or an environment in which the sensor device is arranged for making measurements. Another objective of the present description is to provide a method for manufacturing such a sensor device.

These and other objectives are at least partly met by the invention as defined in the independent claims. Preferred embodiments are set out in the dependent claims.

According to a first aspect, there is provided a sensor device for sensing a property of a biological material, said sensor device comprising: a biocompatible enclosure defining at least one compartment, the biocompatible enclosure comprising a barrier having a first surface and a second surface opposite to the first surface, wherein the barrier is formed from biocompatible and electrically insulating material; at least one sensor receptor element arranged at the first surface of the barrier; an electronic or photonic circuitry comprising at least one sensor transducer element for reading out signals from the at least one sensor receptor element, wherein the electronic or photonic circuitry is arranged at the second surface of the barrier and wherein the at least one sensor receptor element and the at least one sensor transducer element are configured to communicate through the barrier; and wherein the at least one compartment is configured to control transport of the biological material into the compartment or wherein the at least one compartment is configured to form a hermetical seal around the electronic or photonic circuitry; wherein the sensor device is configured to be arranged with the at least one sensor receptor element making contact with the biological material for sensing the property of the biological material and the electronic or photonic circuitry comprising the at least one sensor transducer element being protected from making contact with the biological material.

The electronic or photonic circuitry may be directly arranged at the second surface of the barrier. For instance, conductive patterns may be printed directly on the second surface of the barrier. In addition, the at least one transducer element may be directly bonded to the second surface of the barrier.

However, according to an embodiment, the sensor device may further comprise a substrate carrying the electronic or photonic circuitry.

Thus, according to an embodiment of the first aspect, there is provided a sensor device for sensing a property of a biological material, said sensor device comprising: a biocompatible enclosure defining at least one compartment, the biocompatible enclosure comprising a barrier having a first surface and a second surface opposite to the first surface, wherein the barrier is formed from biocompatible and electrically insulating material; at least one sensor receptor element arranged at the first surface of the barrier; a substrate carrying an electronic or photonic circuitry comprising at least one sensor transducer element for reading out signals from the at least one sensor receptor element, wherein the substrate is arranged at the second surface of the barrier and wherein the at least one sensor receptor element and the at least one sensor transducer element are configured to communicate through the barrier; and wherein the at least one compartment is configured to control transport of the biological material into the compartment or wherein the at least one compartment is configured to form a hermetical seal around the substrate carrying the electronic or photonic circuitry; wherein the sensor device is configured to be arranged with the at least one sensor receptor element making contact with the biological material for sensing the property of the biological material and the electronic or photonic circuitry comprising the at least one sensor transducer element being protected from making contact with the biological material.

Thanks to the sensor device, a biocompatible enclosure is used in order to protect vulnerable parts of the sensor device from making contact with biological material. Thus, the biological material may not be able to damage vulnerable parts of the sensor device such that a long operational lifetime of the sensor device may be achieved.

The sensor device is configured such that parts of the sensor device which may need to make contact with the biological material in order to enable sensing a property of the biological material are able to come into contact with the biological material. Even though contact with the biological material is therefore provided, the sensor device may still ensure that other parts of the sensor device do not make contact with the biological material.

The biocompatible enclosure defines a compartment, which is used for controlling how parts of the sensor device make contact with the biological material.

The biocompatible enclosure may ensure that the compartment forms a hermetical seal around the substrate carrying electronic or photonic circuitry. Thus, the electronic or photonic circuitry is protected to ensure that biological material in an environment in which the sensor device is arranged is not able to pass the biocompatible enclosure. Hence, the electronic or photonic circuitry is protected from being damaged by the biological material.

The biocompatible enclosure providing a hermetical seal may thus enable that the sensor device may be implanted in a human or animal body.

The biocompatible enclosure may ensure that the compartment controls transport of the biological material into the compartment. For instance, the transport of the biological material may be provided by a flow of biological material. The biological material may be provided in liquid form, such as being a body fluid, such that the biological material may be easily transported through a flow. The biological material may alternatively be provided in a liquid solution which may be used for carrying the biological material into the compartment through a flow. It should also be realized that the biological material may be transported into the compartment in other manner.

The sensor device may be configured such that a controlled flow of biological material is provided in relation to the sensor device. The sensor device may be configured such that flow of biological material for which a property is to be sensed may be limited in relation to the sensor device, wherein the flow is exclusively controlled to flow into the compartment.

Thus, the sensor device may be configured such that the biological material may only flow into the compartment. Hence, the at least one receptor element may be arranged in the compartment, whereas the substrate carrying electronic or photonic circuitry is arranged outside the compartment. By controlling the flow of the biological material into the compartment, the biological material may be prevented from making contact with the electronic or photonic circuitry being arranged outside the compartment. This may be used for instance when the sensor device is configured to sense a property of the biological material outside a body. In such case, the flow of the biological material may be well-controlled and the substrate carrying the electronic or photonic circuitry need not necessarily be arranged within a hermetical seal. For instance, the sensor device may be used for sensing a property of blood outside a body, such as during dialysis, or may be used for sensing a property in a bioreactor, wherein the sensor device need not be arranged in the bioreactor. Also, the sensor device may be arranged with the substrate carrying the electronic or photonic circuitry being arranged externally to a body while the compartment for receiving flow of the biological material is arranged subcutaneously in the body.

The sensor device may form a chemical sensor comprising a receptor part, comprising the at least one sensor receptor element, and a transducer part, comprising the at least one sensor transducer element. The receptor part may be configured to transform chemical information into a form of energy which may be measured by the transducer part. The transducer part may be capable of transforming the energy carrying the chemical information into a useful analytical signal.

The sensor device is configured such that the at least one sensor receptor element may make contact with the biological material for sensing a property, while the at least one sensor transducer element is part of the electronic or photonic circuitry prevented from making contact with the biological material. Thus, the at least one sensor receptor element and the at least one sensor transducer element are arranged on opposite sides of the barrier, which prevents biological material at the first surface to reach the second surface opposite to the first surface.

Further, thanks to the at least one sensor receptor element being arranged at the first surface of the barrier, opposite to the second surface of the barrier at which the substrate carrying the electronic or photonic circuitry is arranged, the at least one sensor receptor element may be manufactured separately from the electronic or photonic circuitry. This implies that materials used in the at least one sensor receptor element may be freely chosen and do not need to be compatible with a manufacturing process for manufacturing the electronic or photonic circuitry. In particular, the at least one sensor receptor element may use materials which are not compatible with complementary metal-oxide-semiconductor (CMOS) processing. This implies that the at least one sensor receptor element may be adapted to sense the property of the biological material, without necessarily taking compatibility with CMOS processing into account when designing the at least one sensor receptor element.

As mentioned, the at least one sensor transducer element may be configured to provide a useful analytical signal. Thus, the signal from the at least one sensor transducer element may be further processed by an electronic or photonic circuitry. Therefore, the at least one sensor transducer element may be conveniently arranged as part of the electronic or photonic circuitry for facilitating further processing of the analytical signal.

The at least one sensor receptor element may be configured to sense the property of the biological material in different manners. The at least one sensor element may be configured to sense a physical property representing a property of the biological material, such as sensing an optical property (absorbance, refractive index), an electrical property (conductivity) or a temperature. The at least one sensor element may alternatively be configured to sense a chemical or biochemical property, wherein a chemical reaction or a biochemical process provides chemical information that may be sensed by the at least one sensor receptor element.

The at least one sensor transducer element may be configured to read out information from the at least one sensor receptor element. The at least one sensor transducer element may thus be configured to convert information acquired by the at least one sensor receptor element to an analytical signal. The at least one sensor transducer element may be configured to provide an electrical or optical signal representative of information sensed by the at least one sensor receptor element, which electrical or optical signal is suitable for being further processed by the electronic or photonic circuitry.

According to an embodiment, the at least one sensor receptor element may be selective to a particular analyte of the biological material, such that information acquired by the at least one sensor element is representative of the particular analyte. The at least one sensor transducer element may not be selective to a particular analyte but may rather be able to generically convert information of the at least one sensor receptor element to an analytical signal.

The sensor device may comprise a plurality of sensor receptor elements. Each of the sensor receptor elements may be mutually unique such that different sensor receptor elements may be configured to sense different properties, such as being selective to different analytes of the biological material. Alternatively, some of the sensor receptor elements may be identical for sensing the same property so as to provide a redundancy of sensor receptor elements in the sensor device.

The sensor device may comprise a plurality of sensor transducer element. Each sensor transducer element may be associated with a mutually unique sensor receptor element such that the sensor transducer element may be dedicated to read out signals from a particular sensor receptor element. However, one or more sensor transducer elements may be configured to read out signals from a plurality of sensor receptor elements such that the sensor transducer element may be associated with a plurality of sensor receptor elements.

The biological material may for instance be any organic matter that originates from a living organism, a chemical substance present or produced by a living organism, such as a biomolecule, or a body fluid, such as blood.

It should be realized that even though a flow of biological material is discussed, the biological material itself need not be a fluid. The biological material may be a body fluid, such as blood. However, the biological material need not necessarily be a fluid but could be solved into or carried by a fluid, such as a sterile solution, for allowing flow of the biological material.

The sensor device may be configured to sense any property of the biological material. The sensor device may for instance be configured to sense presence and/or quantity of one or more particular analytes. In this regard, the at least one sensor receptor element may be selective to one or more particular analytes, such as being configured to capture analyte(s) at the sensor receptor element. The sensor device may alternatively be configured to sense a physical property of the biological material, such as an optical or electrical property.

The biocompatible enclosure may be configured to form a biocompatible exterior enclosing the at least one compartment. The biocompatible enclosure may thus be not harmful or toxic to living tissue. This may also imply that the biocompatible enclosure is configured such that it will not be attacked by an active immune system of a human being or animal.

The biocompatible enclosure may be formed entirely by one or more biocompatible materials. It should be realized that different parts of the biocompatible enclosure may be formed by different materials. Alternatively or additionally, an external and/or internal surface of the biocompatible enclosure may be treated, such as to provide a biocompatible interface to biological material. It should be realized that, when flow of biological material is allowed into the compartment, the internal surface of the biocompatible enclosure needs to be biocompatible, whereas when the compartment protects components in the compartment from making contact with the biological material, the external surface of the biocompatible enclosure needs to be biocompatible.

It should further be realized that biocompatibility of the biocompatible enclosure may relate to more than a material of the biocompatible enclosure making contact with biological material. A surface structure of the biocompatible enclosure may also affect biocompatibility regardless of material of the biocompatible enclosure. For instance, the biocompatible enclosure may be configured to provide a smooth surface to provide a biocompatible surface structure.

The barrier of the biocompatible enclosure may be configured to form a side wall or a portion of a side wall of the biocompatible enclosure. The barrier may be configured to separate the first surface of the barrier from the second surface of the barrier, such that the at least one sensor receptor element arranged at the first surface may be configured to be exposed to the biological material without the electronic or photonic circuitry arranged at the second surface being exposed to the biological material.

The barrier is biocompatible such that the first surface of the barrier being exposed to biological material is not harmful or toxic to living tissue and will not be attacked by an active immune system of a human being or animal. The barrier is further formed from an electrically insulating material such that signals between the at least one sensor receptor element and the at least one sensor transducer element may be controlled. Thus, the sensor device may be configured to provide dedicated contacts through the barrier for transporting signals between the at least one receptor element and the at least on sensor transducer element or the sensor device may be configured to provide wireless communication through the barrier.

The biocompatible enclosure may be formed from a single material. Thus, the biocompatible enclosure may be formed from an electrically insulating material. However, it should be understood that the entire biocompatible enclosure need not be formed from the same material. For instance, different walls may be formed from different materials, such that walls of the biocompatible enclosure not forming part of the barrier need not be formed from electrically insulating material.

The biocompatible enclosure may be formed such that no epoxies or other adhesive material are used for bonding walls of the biocompatible enclosure to each other. This implies that there will not be any contact between epoxies and biological material, such as body fluids, which avoids a risk of leakage of residues from epoxies to the biological material and also avoids gradual ingress of biological material through epoxies. This implies that the sensor device may provide a long-term biocompatibility.

The electronic or photonic circuitry may be configured to read out signals from the at least one sensor receptor element using the at least one sensor transducer element. The electronic or photonic circuitry may further be configured to process a signal from the at least one sensor transducer element, such as analyzing the read out signal and/or taking actions in response to the signal from the at least one sensor transducer element. The electronic or photonic circuitry may also or alternatively be configured to store the read out signals for later retrieval, e.g., when the sensor device is no longer arranged in an environment including the biological material. The electronic or photonic circuitry may also or alternatively be configured to communicate the read out signals to an external device, e.g., using a wired or wireless communication with the external device.

It should be realized that the at least one sensor receptor element being arranged at the first surface of the barrier does not necessarily imply that the at least one sensor receptor element is arranged directly on or in direct contact with the first surface of the barrier. While the at least one sensor receptor element may be arranged on the first surface of the barrier, the at least one sensor receptor element may alternatively be arranged in vicinity of the first surface of the barrier, such as being arranged on a protrusion extending from the first surface of the barrier.

Similarly, it should be realized that the substrate being arranged at the second surface of the barrier does not necessarily imply that the substrate is arranged directly on or in direct contact with the second surface of the barrier. Rather, the substrate may be mounted such that it is arranged at the second surface of the barrier by being arranged in close vicinity to the second surface of the barrier.

Additionally, it should be realized that the substrate and the electronic or photonic circuitry can be integrated in a single structure. For instance, the substrate and the electronic or photonic circuitry may be formed as a printed circuit board (PCB) comprising discrete electronic elements or a silicon integrated circuit.

According to an embodiment, the biocompatible enclosure is formed from glass. Glass is a biocompatible material. Using glass for forming the biocompatible enclosure, walls of the biocompatible enclosure may be separately formed and bonded together to form an enclosure which defines the compartment without using any epoxies or other adhesive material for bonding the separately formed walls.

The use of separately formed walls may facilitate assembling different parts of the sensor device while providing a biocompatible enclosure defining the at least one compartment.

It should however be realized that other materials may be used instead or in addition to glass. The biocompatible enclosure may alternatively be formed from silicon oxide, aluminum oxide, such as high purity alumina ($Al_2O_3$), magnesium oxide, titanium oxide, zirconium oxide, such as high purity zirconia ($ZrO_2$), silicon carbide, silicon nitride, ceramics, or quartz, or from any combination of these materials.

According to another embodiment, at least the barrier of the biocompatible enclosure is formed from glass, silicon oxide, aluminum oxide, such as high purity alumina ($Al_2O_3$), magnesium oxide, titanium oxide, zirconium oxide, such as high purity zirconia ($ZrO_2$), silicon carbide, silicon nitride, ceramics, or quartz. Thus, the barrier is formed from an electrically insulating material.

However, it should be realized that other parts of the biocompatible enclosure than the barrier need not be formed from an electrically insulating material, such that the biocompatible enclosure may comprise walls formed from titanium, such as pure titanium (type T40), platinum iridium (Pt/Ir 90/10), pure platinum, niobium, or stainless steel. For example, a ceramic barrier may be bonded to a titanium enclosure by gold brazing at high temperature, typically at 1000° C. or higher.

According to an embodiment, the barrier of the biocompatible enclosure comprises through-going holes, wherein the through-going holes are filled by a conducting material for providing electrical contact between the at least one sensor receptor element and the at least one sensor transducer element.

Thus, communication between the at least one sensor receptor element and the at least one sensor transducer element may be provided by an electrical contact extending through the barrier.

For example, the transducer element may comprise circuitry for electrical impedance spectroscopy read-out or potentiostat circuitry for electrochemical read-out, including potentiometry, voltammetry or amperometry methods, or an extended gate field-effect transistor for surface charge read-out.

The conducting material may be any material suitable for transporting an electrical signal. The conducting material may typically comprise tungsten, gold, or copper, which is commonly used as metal interconnects in integrated circuits. The conducting material need not be formed by a same material used in the at least one sensor receptor element. The at least one sensor receptor element may use a material adapted for sensor performance.

The at least one sensor receptor element may be arranged to cover the through-going holes. This implies that the through-going holes filled by conducting material will not be directly exposed to the biological material such that any deterioration of the conducting material based on exposure to biological material may be prevented.

According to another embodiment, the at least one sensor transducer element is configured to transmit an interrogation electromagnetic signal through the barrier to the at least one sensor receptor element and for receiving a response signal from the at least one sensor receptor element.

Thus, the at least one sensor transducer element and the at least one sensor receptor element may communicate through wireless communication. The interrogation electromagnetic signal may be a light signal, such as using ultraviolet, visible, or infrared light. The at least one sensor transducer element may be arranged in a photonic integrated circuit providing processing and/or transport of optical signals. The at least one sensor transducer element may alternatively be arranged in an electronic circuitry, which may be configured to process and/or transport electrical signals based on optical interrogation of the at least one sensor receptor element.

The at least one sensor transducer element may comprise a light emitting diode (LED) or any other light source for generating the interrogation electromagnetic signal in the form of a light signal. Alternatively, the at least one sensor transducer element may receive the light signal from a LED or other light source. The at least one sensor transducer element may further comprise a photodetector for detecting the response signal from the at least one sensor receptor element. The at least one sensor transducer element may be configured to convert a detection of the response signal to an electrical signal, which may be further provided to the electronic circuitry. Alternatively, the at least one sensor transducer element may provide an optical signal based on detection of the response signal, wherein the optical signal is provided to the photonic circuitry.

The interrogation electromagnetic signal may alternatively use another frequency, which is not optical, so as to enable communicating for example through capacitive or inductive communication. For instance, the communication between the at least one sensor transducer element and the at least one sensor receptor element may then use a signal frequency in a range of 10 mHz-1 GHz. The at least one sensor transducer element may thus receive a response signal representative of an electrical property of the at least one sensor receptor element, such as a response signal representative of a potential, charge, or impedance of the at least one sensor receptor element.

According to an embodiment, the barrier of the biocompatible enclosure is a first wall and wherein the sensor device further comprises a second wall formed from biocompatible material, wherein the second wall is arranged facing the first surface of the first wall and the second wall comprises a membrane area comprising a plurality of through-going openings through the second wall for selectively passing biological material through the second wall.

Thus, the biocompatible enclosure may define a compartment configured to receive the biological material into the compartment, wherein the first wall and the second wall oppose each other.

The biological material may be controlled to flow towards the membrane area for passing through the second wall in order for the biological material to reach the at least one sensor receptor element.

Thanks to the membrane area comprising through-going openings, a size of the through-going openings may be used for controlling biological material that is allowed to pass the second wall and to reach the at least one sensor receptor element. For instance, the through-going openings may have a size in a micrometer range, such as defining openings through the membrane area having a size in a range of 1-100 μm, such as 5-20 μm or 5-10 μm. This implies that the membrane area may prevent cells from passing the second wall.

The second wall may be formed from a biocompatible material. However, the second wall need not necessarily be formed from a same material as the barrier or even other walls of the biocompatible enclosure.

The second wall may be formed from glass, which is a suitable biocompatible material.

However, the second wall may be formed from another material, which may facilitate forming small through-going openings, such as through-going openings having a size smaller than 1 μm. For instance, the second wall may be formed from silicon, which may facilitate forming small through-going openings. Such a second wall may for instance be anodically bonded to a glass layer of the biocompatible enclosure or may be anodically bonded to a glass carrier substrate which carries the second wall, and which may in turn be bonded to glass layers forming other walls of the biocompatible enclosure. Alternatively, the silicon second wall may be thermally bonded to a titanium enclosure using gold paste at moderate temperature below 400° C.

Alternatively, the second wall may be formed from a metal mesh. Such a second wall may for instance be thermally bonded to a glass layer of the biocompatible enclosure.

According to an embodiment, the sensor device further comprises a protective coating on the membrane area for protecting the through-going openings from being blocked.

The protective coating may thus ensure that through-going openings of the membrane do not get blocked over time when the sensor device is used. In particular, the protective coating may prevent adsorption of proteins to a surface of the membrane area. Protection against adsorption of proteins or other particles in the biological material, such as a body fluid, may be referred to as antifouling protection. Examples of protective coatings are hydrophilic polymer grafting coatings, comprising polyethylene glycol or zwitterionic carboxybetaine moieties.

Thus, the protective coating may be useful in ensuring a long operational lifetime of the sensor device.

According to an embodiment, the sensor device further comprises a protein filter on or below the membrane area for selectively excluding protein access to the at least one sensor element.

The protein filter may be attached to the membrane area. The protein filter may be attached at a surface of the membrane area facing the first surface of the first wall or at an opposite surface of the membrane area.

The protein filter may enable filtering based on a smaller size of particles than the filtering of the membrane area. Thus, the protein filter may define pore sizes smaller than 50 nm, such as smaller than 10 nm. Pores of the protein filter may selectively prevent particular proteins from passing the protein filter, such that the proteins are not allowed to reach the at least one sensor receptor element.

The sensor device enables antifouling protection and protein filtering separate from the at least one sensor receptor element. Thus, the protection is not provided at a surface of the at least one sensor receptor element but rather prevents undesired proteins (or other substances) at an entry of the biological material through the membrane area. This implies that the antifouling protection and protein filtering may be separately optimized independently of the at least one sensor receptor element, such as materials used for the at least one sensor receptor element.

The protein filter may be formed from a material suitable for forming small pore sizes. The protein filter may for instance be formed in silicon, silicon oxide or aluminum oxide. The protein filter may be formed using lithography, acid etching, thermal oxidation, or anodization to form the pores of the protein filter.

According to an embodiment, the second wall is arranged as an internal wall within a compartment of the at least one compartment configured to control transport of the biological material into the compartment, wherein the second wall separates the compartment into two sub-compartments and is configured to provide fluid communication between the two sub-compartments through the membrane area.

Thus, the sensor device may be configured to control flow of biological material into and out of a first sub-compartment. The first sub-compartment may then be connected to a second sub-compartment, wherein the first and second sub-compartments are separated by a membrane area and, possibly also a protein filter. Thus, the first sub-compartment may be designed in order to control flow of biological material, such that the first sub-compartment may define inlet opening(s) and outlet opening(s) through which the biological material may flow. However, the membrane area and/or protein filter may be designed to control which particles are allowed to enter the second sub-compartment in which the at least one sensor receptor element is arranged and may therefore be independently designed from the inlet opening(s) and outlet opening(s).

According to an embodiment, the at least one compartment comprises a first compartment configured to control flow of the biological material into the first compartment, wherein the biocompatible enclosure comprises an inlet opening for allowing flow of the biological material into the first compartment and an outlet opening for allowing flow of the biological material out of the first compartment.

The at least one sensor receptor element may be arranged within the first compartment and the at least one sensor receptor element may thus be arranged within the biocompatible enclosure.

According to an embodiment, the at least one compartment may further comprise a second compartment configured to form a hermetical seal around the substrate carrying the electronic circuitry.

Thus, the biocompatible enclosure may define two compartments, such that the biocompatible enclosure both i) controls flow of biological material in order for controlling the biological material reaching the at least one sensor receptor element and ii) ensures that the electronic or photonic circuitry is protected from making contact with the biological material. This implies that the sensor device is suitable for many different applications, including that the sensor device may be arranged implanted in a human or animal body.

According to an embodiment, the sensor device comprises a plurality of stacked plates forming a stack with the stacked plates bonded to each other at edges of the sensor device, wherein the stacked plates include at least a first plate carrying the at least one sensor receptor element, a second plate for defining a spacing, and a third plate, wherein the first plate, the second plate and the third plate are bonded together to form the biocompatible enclosure with the second plate defining a spacing between the first plate and the third plate.

The use of stacked plates may facilitate that the sensor device may be easily manufactured, and that the sensor device may be manufactured in large scale with a large number of sensor devices being manufactured simultaneously using wafer-level processing. Thanks to stacking of plates, individual components of the sensor device may be separately manufactured, such that manufacturing of an individual component need not be restricted to manufacturing requirements of other individual components (such as materials and temperatures of manufacturing steps). The individually formed plates may then be joined together to form the sensor device when the plates are stacked and bonded together.

The plates may define interior walls associated with different sensor devices. Thus, the plates may be bonded to each other at each of a plurality of interior walls for simultaneously defining a plurality of sensor devices. Thus, the edge of the sensor device may be formed by interior walls of the plates.

Each of the stacked plates may be formed by a same material, such as glass. This facilitates bonding of the plates to each other for forming a proper biocompatible enclosure. For instance, no epoxies or other adhesive material may be needed for attaching the plates to each other. Rather, bonding of the plates may be provided, e.g., by laser welding the plates to each other so as to form a biocompatible enclosure of a homogeneous material.

The first plate may form the barrier of the biocompatible enclosure and may form a bottom surface of a compartment defined by the biocompatible enclosure. The second plate may define side walls of the compartment and the third plate may define a top surface of the compartment. It should be realized that further plates may be used when the sensor device comprises further layers.

According to an embodiment, the at least one sensor receptor element comprises carbon, graphene, gold, silver, platinum and/or conductive polymer.

Such materials may be suitable for providing electrodes and/or field effect transistor channels for electrochemical sensing of a property of the biological material. Thanks to the at least one sensor receptor element being separated from the electronic or photonic circuitry by the barrier and the at least one sensor receptor element being able to be separately manufactured from the electronic or photonic circuitry, manufacturing of the at least one sensor receptor element need not take into account restrictions in relation to manufacturing of the electronic or photonic circuitry.

Therefore, even though carbon, gold, silver and platinum are typically not compatible with CMOS processing, the at least one sensor receptor element may still be formed comprising carbon, gold, silver, and/or platinum.

According to an embodiment, the at least one sensor receptor element is configured to capture an analyte of interest.

Thus, the at least one sensor receptor element may be selective for sensing a particular analyte. Thus, the sensor device may be configured for selective sensing of the analyte.

The sensor device may comprise a first set of sensor receptor elements, wherein different sensor receptor elements in the first set are configured to capture different analytes of interest. Thus, the sensor device may be configured for selective sensing of a plurality of analytes.

The sensor device may also comprise a second set of sensor receptor elements, wherein each of the sensor receptor elements in the second set are configured to capture the same analyte of interest. Thus, the sensor device may provide redundancy of sensor receptor elements such that the sensor device may still be operational even if one sensor receptor element stops working.

The sensor device may comprise one or more of the first set and/or the second set of sensor receptor elements. Thus, the sensor device may for instance provide redundancy for selective sensing of a plurality of analytes.

The at least one sensor receptor element may comprise materials for selective interaction with specific target analytes. For instance, the at least one sensor receptor element may comprise ion selective membranes, ion exchange membranes, ionophores, enzymes, antibodies, nanobodies, DNA, aptamers, molecularly imprinted polymers, organelles, cells, or optically active materials, like fluorophores, phosphors, electrochemiluminescent or photoelectrochemical materials, or surface plasmon metal films.

According to an embodiment, the sensor device is configured to be at least partly implantable in a human or animal body.

This implies that the sensor device may be configured to provide sensing of a property of a biological material when implanted in the human or animal body. Thanks to the sensor device providing a biocompatible enclosure, the sensor device may be compatible with being at least partly implantable such that the sensor device may be used for long-term operation while being at least partly implanted.

According to an embodiment, a system may comprise a plurality of sensor devices. The sensor devices in the plurality of sensor devices may be configured to be arranged in different locations for sensing a property of the biological material. The sensor devices may be configured to provide measurement information of the property sensed by respective sensor devices to a common processing unit of the system.

The system may thus allow monitoring of a process relating to the property of the biological material. For instance, the plurality of sensor devices may be arranged to sense a property of blood before and after dialysis. The common processing unit receiving input from the plurality of sensor devices may thus be able to analyze functionality of a dialysis apparatus or functionality of a kidney in a human body. For instance, the processing unit may be able to determine whether toxins are properly removed from the blood by the dialysis apparatus or by the kidney.

According to a second aspect, there is provided a method for manufacturing a sensor device for sensing a property of a biological material, said method comprising: stacking at least three plates, each formed of biocompatible material, wherein a first plate of the at least three plates comprises a barrier formed from biocompatible and electrically insulating material, wherein the barrier has a first surface and a second surface opposite to the first surface and wherein at least one sensor receptor element is arranged at the first surface of the barrier; arranging an electronic or photonic circuitry at the second surface of the barrier, wherein the electronic or photonic circuitry comprises at least one sensor transducer element for reading out signals from the at least one sensor receptor element by communication through the barrier, bonding edges of at least one sensor device in the at least three plates to each other so as to form a biocompatible enclosure defining at least one compartment, wherein the biocompatible enclosure comprises the barrier of the first plate and wherein the at least one compartment is configured to control transport of the biological material into the compartment or wherein the at least one compartment is configured to form a hermetical seal around the electronic or photonic circuitry.

The electronic or photonic circuitry may be directly arranged at the second surface of the barrier. For instance, conductive patterns may be printed directly on the second surface of the barrier. In addition, the at least one transducer element may be directly bonded to the second surface of the barrier.

However, according to an embodiment, the arranging of an electronic or photonic circuitry at the second surface of the barrier comprises arranging a substrate at the second surface of the barrier, wherein the substrate carries the electronic or photonic circuitry.

Thus, according to an embodiment of the second aspect, there is provided a method for manufacturing a sensor device for sensing a property of a biological material, said method comprising: stacking at least three plates, each formed of biocompatible material, wherein a first plate of the at least three plates comprises a barrier formed from biocompatible and electrically insulating material, wherein the barrier has a first surface and a second surface opposite to the first surface and wherein at least one sensor receptor element is arranged at the first surface of the barrier; arranging a substrate at the second surface of the barrier, wherein the substrate carries an electronic or photonic circuitry comprising at least one sensor transducer element for reading out signals from the at least one sensor receptor element by communication through the barrier, bonding edges of at least one sensor device in the at least three plates to each other so as to form a biocompatible enclosure defining at least one compartment, wherein the biocompatible enclosure comprises the barrier of the first plate and wherein the at least one compartment is configured to control transport of the biological material into the compartment or wherein the at least one compartment is configured to form a hermetical seal around the substrate carrying the electronic or photonic circuitry.

Effects and features of this second aspect are largely analogous to those described above in connection with the first aspect. Embodiments mentioned in relation to the first aspect are largely compatible with the second aspect.

Thanks to the manufacturing of the sensor device, a biocompatible enclosure is formed which may be used for protecting vulnerable parts of the sensor device from making contact with biological material. Thus, the biological material may not be able to damage vulnerable parts of the sensor device such that a long operational lifetime of the sensor device may be achieved.

The sensor device is manufactured such that parts of the sensor device which may need to make contact with the biological material in order to enable sensing a property of the biological material are able to come into contact with the biological material. Even though contact with the biological material is therefore provided, the sensor device may still ensure that other parts of the sensor device do not make contact with the biological material.

The manufacturing of the sensor device allows the three plates and the substrate carrying the electronic or photonic circuitry to be separately manufactured. This implies that manufacturing of each of the parts of the sensor device may be individually optimized and need not take into account restrictions on manufacturing of other parts.

The manufacturing of the sensor device may allow manufacturing of a plurality of sensor devices in parallel using wafer-level processing. Thus, sensor devices may be efficiently manufactured at low manufacturing costs.

According to an embodiment, bonding of the edges comprises laser welding the edges for forming a bond.

The plates may be formed from glass, which enables use of laser welding for bonding of the plates. Alternatively, the plates may be composed of titanium, which also enable use of laser welding for hermetically sealing and connecting the titanium plates.

The bonding of the edges may be achieved without use of any epoxies or other adhesive materials. This implies that the sensor device is manufactured without epoxies so contact between epoxies and biological material, such as body fluids, during use of the sensor device may be prevented. This avoids the risk of leakage of residues from the epoxies to the biological material and also avoids gradual ingress of biological material through epoxies. This implies that the sensor device may be manufactured to provide a long-term biocompatibility of the sensor device.

BRIEF DESCRIPTION OF THE DRAWINGS

The above, as well as additional objects, features, and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Figure 1:
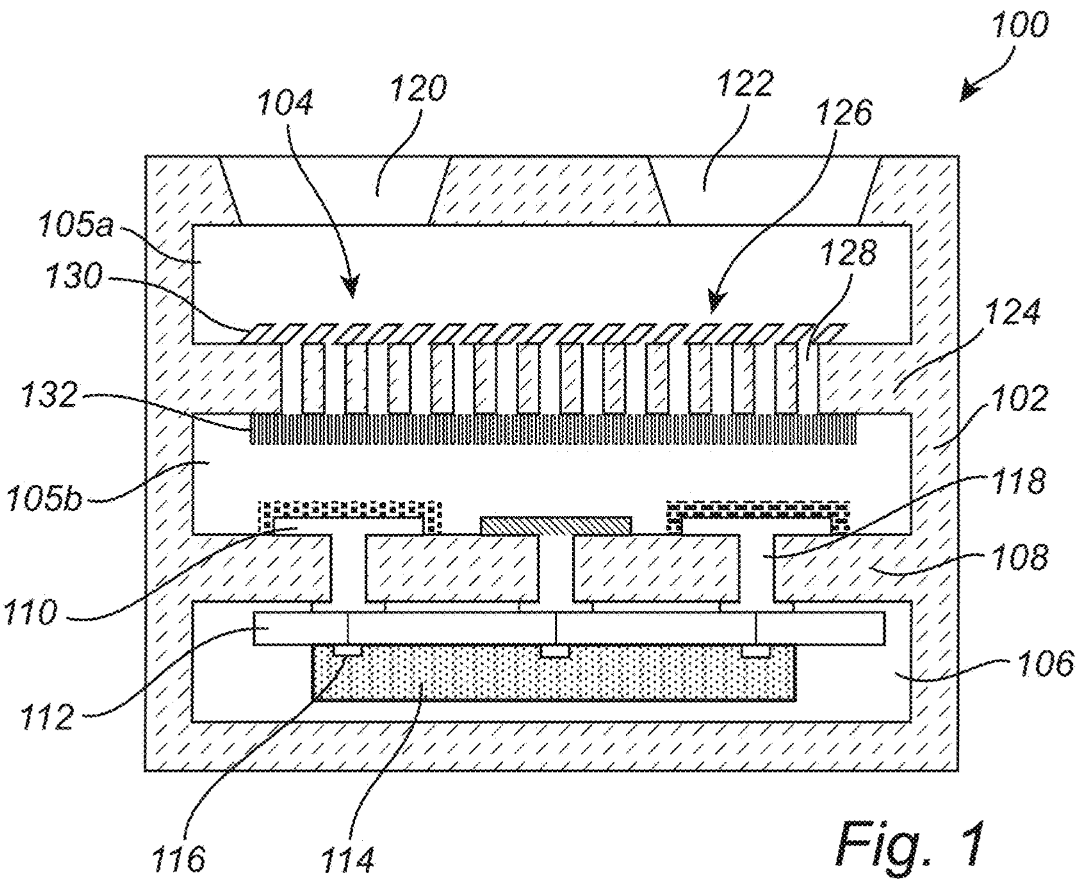
FIG. 1 is a schematic view of a cross-section of a sensor device according to a first embodiment.

Referring now to FIG. 1, a sensor device 100 according to a first embodiment will be described.

The sensor device 100 comprises a biocompatible enclosure 102 defining a first compartment 104 and a second compartment 106. The biocompatible enclosure 102 comprises a barrier 108 separating the first compartment 104 from the second compartment 106. The barrier 108 may thus form a wall or part of a wall of the first compartment 104 as well as the second compartment 106.

The biocompatible enclosure 102 is formed from a biocompatible material, such as glass, silicon oxide, aluminum oxide, magnesium oxide, titanium oxide, zirconium oxide, silicon carbide, silicon nitride, ceramics, or quartz.

The biocompatible enclosure 102 may be formed from a homogeneous material or different parts of the biocompatible enclosure 102 may be formed from different materials.

The barrier 108 may be formed from a biocompatible and electrically insulating material. The barrier 108 may be formed from a same material as other parts of the biocompatible enclosure 102 or may be formed from another material than other parts of the biocompatible enclosure 102. The barrier 108 may be formed from glass, silicon oxide, aluminum oxide, magnesium oxide, titanium oxide, zirconium oxide, silicon carbide, silicon nitride, ceramics, or quartz.

According to an embodiment, the barrier 108 is formed from glass. The entire biocompatible enclosure 102 may be formed from glass, preferably borosilicate glass, which is a suitable biocompatible material, and which may also allow for the sensor device 100 to be formed by separately manufactured plates that may be attached together, e.g., by laser welding.

According to another embodiment, the barrier 108 may be a ceramic barrier, which may be bonded to a titanium enclosure such that the barrier 108 is surrounded by the titanium enclosure at edges of the barrier 108. The ceramic barrier may be bonded to the titanium enclosure by gold brazing at high temperature, typically at 1000° C. or higher. The bonding of the ceramic barrier to the titanium enclosure may be performed before the barrier 108 is assembled with other parts of the sensor device 100 such that the high temperature treatment will not affect other components of the sensor device 100.

The titanium enclosure may be attached to further walls formed from titanium allowing the biocompatible enclosure 102 of the sensor device 100 to be assembled using a procedure that does not affect components of the sensor device 100, such as using laser welding.

The sensor device 100 may comprise at least one sensor receptor element 110 arranged at a first surface of the barrier 108. The at least one sensor receptor element 110 may thus be arranged within the first compartment 104.

The sensor device 100 may further comprise a substrate 112 carrying an electronic or photonic circuitry 114. The substrate 112 is arranged at a second surface of the barrier 108, opposite to the first surface, and may thus be arranged within the second compartment 106.

The at least one sensor receptor element 110 may be configured to make contact with a biological material for sensing a property of the biological material. Thus, the biological material may be allowed to enter the first compartment 104. However, the substrate 112 carrying the electronic or photonic circuitry 114 may be arranged in the second compartment 106 and the barrier 108 may function to prevent the biological material present in the first compartment 104 to reach the second compartment 106. Further, the biocompatible enclosure 102 may form a hermetical seal of the second compartment 106 such that a hermetical seal is formed around the substrate 112 carrying the electronic or photonic circuitry 114. This implies that the electronic or photonic circuitry 114 may be protected from making contact with the biological material.

The at least one sensor receptor element 110 may be configured to sense a desired property of the biological material. The at least one sensor receptor element 110 may for instance be selective to a particular analyte of the biological material, such that information acquired by the at least one sensor element 110 is representative of the particular analyte. The at least one sensor receptor element 110 may for instance comprise materials for selective interaction with specific target analytes. For instance, the at least one sensor receptor element 110 may comprise ion selective membranes, ion exchange membranes, ionophores, enzymes, antibodies, nanobodies, DNA, aptamers, molecularly imprinted polymers, organelles, cells, or optically active materials, like fluorophores, phosphors, electrochemiluminescent or photoelectrochemical materials, or surface plasmon metal films.

The at least one sensor receptor element 110 may further comprise an electrode. The electrode may be configured to acquire an electrical signal such as an electrical charge, potential or current or to generate an optical signal in dependence of the property of the biological material, such as in dependence of an amount of analytes being captured by the at least one sensor element 110. A surface of the electrode may be treated with a material for selective interaction with target analyte(s).

The electrode of the at least one sensor receptor element 110 may be formed from carbon, graphene, gold, silver, platinum or conductive polymer, e.g., poly(3,4-ethylenedioxythiophene) polystyrene sulfonate (PEDOT:PSS). Such materials are particularly suitable for use in an electrode and/or field effect transistor channel for selective sensing of target analytes. Thanks to the at least one sensor receptor element 110 being separated by the barrier 108 from the substrate 112, the at least one sensor receptor element 110 may be separately manufactured from the substrate 112, such that a choice of materials for the electrode is not dependent on materials compatible with processing of the substrate carrying the electronic or photonic circuitry 114. In particular, the at least one sensor receptor element 110 may comprise materials not compatible with complementary metal-oxide-semiconductor (CMOS) processing, which facilitates use of carbon, gold, silver and/or platinum in the at least one sensor receptor element 110.

The electronic or photonic circuitry 114 comprises at least one sensor transducer element 116. The at least one sensor receptor element 110 and the at least one sensor transducer element 116 are configured to communicate through the barrier 108. Thus, the at least one sensor transducer element 116 may be configured to read out signals from the at least one sensor receptor element 110 for reading out measurements of the property of the biological material.

The at least one sensor transducer element 116 may be configured to communicate with the at least one sensor receptor element 110 through an electrical contact between the at least one sensor transducer element 116 and the at least one sensor receptor element 110. The barrier 108 may in this regard comprise through-going holes filled by a conducting material 118. The through-going holes may extend from the first surface of the barrier 108 to the second surface of the barrier 108.

The at least one sensor receptor element 110 may be connected to the conducting material 118 at the first surface of the barrier 108, such as being arranged immediately above the conducting material 118. The at least one sensor transducer element 116 may be connected to the conducting material 118 at the second surface of the barrier 108.

The substrate 112 may be arranged at the second surface of the barrier 108 such that the at least one transducer element 116 is brought in electrical contact with the conducting material 118 at the second surface of the barrier 108. Thus, the substrate 112 may be mounted in direct contact with the second surface of the barrier 108.

However, the substrate 112 may alternatively be mounted to another structure for defining a location of the substrate 112. For instance, the substrate 112 may be mounted to a plate, which is connected to the barrier 108 when the second compartment 106 is formed. This implies that the substrate 112 may be mounted close to the second surface of the barrier 108 but not necessarily in direct contact with the barrier 108. Then, the at least one sensor transducer element 116 may form an electrical contact with the conducting material 118 by the conducting material 118 protruding slightly from the second surface of the barrier 108 or by forming a connection between the at least one sensor transducer element 116 and the conducting material 118 using solder bumps, conductive epoxy, or ball grid arrays.

According to an alternative embodiment, the electronic or photonic circuitry 114 and the at least one sensor transducer element 116 may be arranged on a chip, such as an application-specific integrated circuit (ASIC) chip forming the substrate 112. The chip may be mounted to the second surface of the barrier 108, e.g., using solder bumps, conductive epoxy, or ball grid arrays, such that the at least one transducer element 116 is brought in electrical contact with the conducting material 118 at the second surface of the barrier 108.

According to another alternative embodiment, the electronic or photonic circuitry 114 may be directly arranged on the second surface of the barrier 108, such as using gold conductive patterns printed directly on a glass surface of the barrier 108. The at least one transducer element 116 may be bonded to the second surface of the barrier 108 to form electrical contact with the conducting material 118 at the second surface of the barrier 108.

The at least one sensor transducer element 116 may be configured to read out information from the at least one sensor receptor element 110 through the communication between the at least one sensor transducer element 116 and the at least one sensor receptor element 110. The at least one sensor transducer element 116 may thus be configured to convert information acquired by the at least one sensor receptor element 110 to an analytical signal.

The at least one sensor transducer element 116 may be configured to provide an electrical or optical signal representative of information sensed by the at least one sensor receptor element 110, which electrical or optical signal is suitable for being further processed by the electronic or photonic circuitry 114. When the at least one sensor transducer element 116 communicates with the at least one sensor receptor element 110 using the conducting material 118 through the barrier 108, the at least one sensor transducer element 116 may be configured to provide an electrical signal to an electronic circuitry 114.

The electronic or photonic circuitry 114 may be configured to process the analytical signal received from the at least one signal transducer element 116. Thus, the electronic or photonic circuitry 114 may comprise a processing unit for processing the analytical signal.

The electronic or photonic circuitry 114 may also or alternatively be configured to store information, such as storing data based on the analytical signal. The electronic or photonic circuitry 114 may also or alternatively be configured to communicate with an external device, such as communicating the analytical signal to the external device. The electronic or photonic circuitry 114 may be configured to provide communication with the external device through wireless communication.

The biocompatible enclosure 102 may be configured to control transport of the biological material into the first compartment 104. The sensor device 100 may thus be configured to allow biological material to enter the first compartment 104 in which the at least one sensor receptor element 110 is arranged.

The biocompatible enclosure 102 may define an inlet opening 120 and an outlet opening 122 in a wall of the biocompatible enclosure 102, whereby biological material may be allowed to pass into the first compartment 104 through the inlet opening 120 and allowed to pass out of the first compartment 104 through the outlet opening 122. Thus, the arrangement of the inlet opening 120 and the outlet opening 122 controls flow into the first compartment 104 by defining a physical location in which flow of the biological material may occur.

The biocompatible enclosure 102 may be configured to be arranged within the biological material, such as being implanted in a human or animal body or being arranged in a reservoir comprising the biological material, such as a bioreactor. The flow of the biological material into the first compartment 104 may occur merely by the sensor device 100 being arranged in contact with, such as surrounded by the biological material.

The sensor device 100 may comprise or may be connected to conduits or channels. Such conduits or channels may be connected to the inlet opening 120 and the outlet opening 122, respectively, of the biocompatible enclosure 102. The flow of biological material may thus occur through the conduits or channels providing a well-controlled flow of biological material into and out of the first compartment 104. This may be useful, for instance, when the sensor device 100 is intended to be used outside a human or animal body, wherein the biological material may be brought to the sensor device 100 through the conduits or channels. However, it could also be used when the sensor device 100 is implanted in a human or animal body in order to control particular flow of biological material into the first compartment 104 such as controlling flow of blood from a kidney into the first compartment 104.

The sensor device 100 comprises an internal wall 124 within the first compartment 104. The internal wall 124 separates the first compartment 104 into a first sub-compartment 105*a* and a second sub-compartment 105*b*. The internal wall 124 may further be used for controlling transport between the first sub-compartment 105*a* and the second sub-compartment 105*b*.

The first sub-compartment 105*a* may comprise the inlet opening 120 and the outlet opening 122 so as to receive flow of biological material. The internal wall 124 may be configured to selectively allow particles or substances to pass through the internal wall 124 such that a filtering of the biological material is provided by the internal wall 124 into the second sub-compartment 105*b*.

The internal wall 124 comprises a membrane area 126 comprising a plurality of through-going openings 128 through the internal wall 124. The through-going openings 128 may define sizes of openings so as to selectively pass biological material through the internal wall 124.

The internal wall 124 may be configured to face the barrier 108 on an opposite side of the barrier 128 in the second sub-compartment 105*b*. Thus, the internal wall 124 may provide a membrane area 126 acting as a filter for a transport of biological material for entering the second sub-compartment 105*b*. The at least one sensor receptor element 110 may then be arranged at a bottom of the second sub-compartment 105*b*.

The through-going openings 128 may have a size for preventing cells of the biological material to enter the second sub-compartment 105*b*. Thus, the through-going openings 128 may have a size in a range of 1-100 μm, such as 5-20 μm or 5-10 μm. This implies that the membrane area 126 may prevent cells or particular types of cells from passing the internal wall 124.

The internal wall 124 may be formed from a biocompatible material. The internal wall 124 may for instance be formed from the same biocompatible material as other parts of the biocompatible enclosure 102. However, it should be realized that the internal wall 124 may be formed from another material than other parts of the biocompatible enclosure 102.

For instance, the internal wall 124 may be formed from glass. If glass is used, the through-going openings 128 may typically be in a micrometer range, since it is difficult to form smaller openings in glass.

According to another embodiment, the internal wall 124 may be formed from another material, such as silicon. In such case, the through-going openings 128 may be even smaller than 1 μm.

For instance, the internal wall 124 may be formed from silicon, wherein the internal wall 124 is surrounded by a titanium enclosure arranged at edges of the internal wall 124. The internal wall 124 may be bonded to the titanium enclosure using gold paste at a moderate temperature below 400° C. This may be particularly useful when the ceramic barrier 108 surrounded by a titanium enclosure, described above, is used. Then, the titanium enclosure of the barrier 108 and the titanium enclosure of the internal wall 124 may be bonded to each other for assembly of the biocompatible enclosure 102. The titanium enclosures may be bonded to each other using laser welding, which implies that only local heating at a point of a laser weld is provided such that components of the sensor device 100 are not damaged by the bonding of the titanium enclosures.

The membrane area 126 may be provided with a protective coating 130. The protective coating 130 may be arranged above the membrane area 126 on a surface of the membrane area 126 facing the first sub-compartment 105*a*. The protective coating 130 may be arranged directly on the membrane area 126.

The protective coating 130 may function as an antifouling coating to protect the through-going openings 128 from being blocked, e.g., due to protein adsorption to the membrane area 126. Thus, the protective coating 130 may reduce fouling of the membrane area 126. However, it should be realized that the protective coating 130 may not be needed or necessarily used.

The sensor device 100 may further comprise a protein filter 132 on or below the membrane area 126. The protein filter 132 may thus be arranged above the membrane area 126 on a surface of the membrane area 126 facing the first sub-compartment 105*a* or below the membrane area 126 on a surface facing the second sub-compartment 105*b*.

The protein filter 132 may be configured to selectively exclude protein access to the second sub-compartment 105*b* in which the at least one sensor element 110 is arranged. The protein filter 132 may be configured to selectively exclude particular proteins or to generally exclude proteins from accessing the second sub-compartment 105*b*.

The protein filter 132 may provide filtering of the biological material based on size of pores of the protein filter 132. The protein filter 132 may be provided with pores defining very small openings through the protein filter 132, such as having pore sizes smaller than 50 nm, such as smaller than 10 nm.

It should be realized that, in some embodiments, there is no need for filtering of proteins for excluding entry of proteins into the second sub-compartment 105*b*. Thus, the protein filter 132 may not be needed or necessarily used.

The sensor device 100 may be formed from a plurality of stacked plates forming a stack with the stacked plates bonded to each other at edges of the sensor device 100. Each layer in the sensor device 100 may be formed from a separate plate, wherein the plates define walls of the sensor device 100 extending throughout the layer or define side walls forming spacer elements so as to allow defining compartments 104, 106 in the sensor device 100.

The at least one sensor receptor element 110 may be formed on a first plate that carries the at least one sensor receptor element 110. The sensor device 100 may further comprise a second plate and a third plate, wherein the second plate defines a spacing between the first plate and the second plate when the plates are bonded together for forming a compartment 104, 106 of the sensor device 100.

The biocompatible enclosure 102 may be formed from a single material such that a same biocompatible material may be used for all plates. This may facilitate bonding of the plates together. However, it should be realized that different materials may be used for different plates.

The sensor device 100 is suited for being implantable in a human or animal body. An entire exterior surface of the sensor device 100 may be defined by a biocompatible material such that the sensor device 100 will not be attacked by an active immune system of the human being or animal in which the sensor device 100 is implanted.

Figure 2:
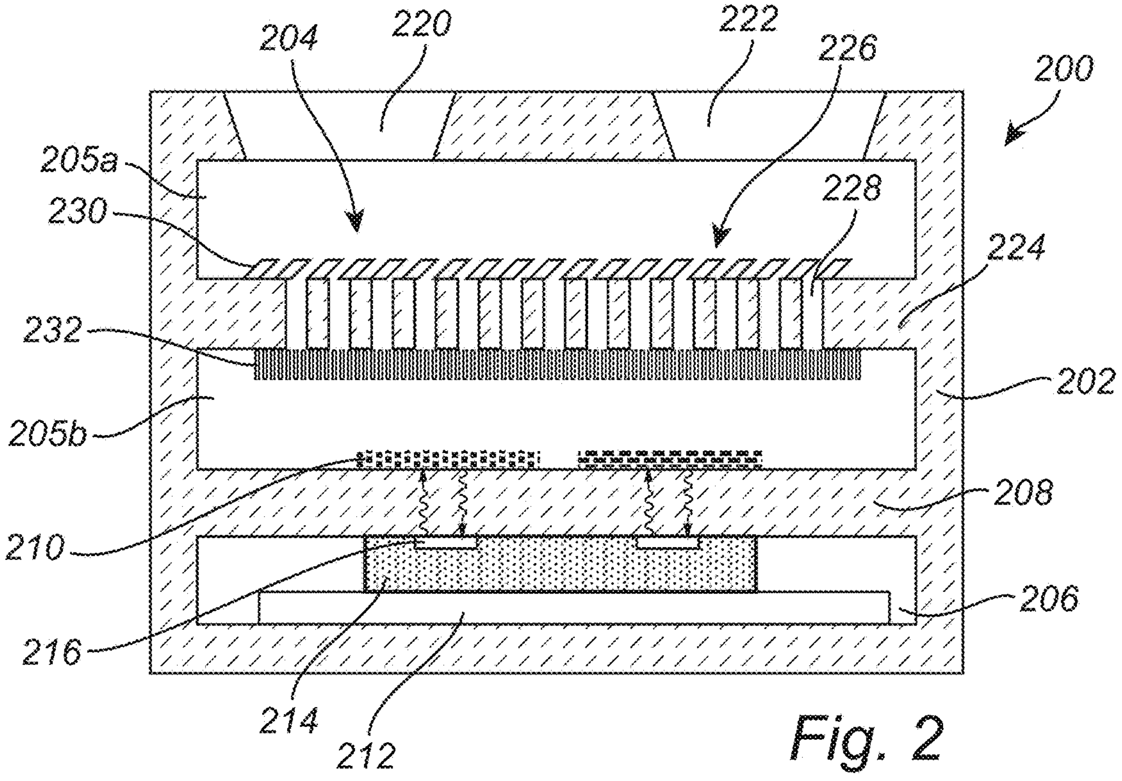
FIG. 2 is a schematic view of a cross-section of a sensor device according to a second embodiment.

Referring now to FIG. 2, a sensor device 200 according to a second embodiment will be described.

The sensor device 200 has many features in common with the sensor device 100 of the first embodiment. Only the features differing from the first embodiment will be discussed in detail.

Thus, the sensor device 200 may comprise a biocompatible enclosure 202 defining a first compartment 204, with a first sub-compartment 205*a* and a second sub-compartment 205*b*, and a second compartment 206. The sensor device 200 may comprise a substrate 212 carrying an electronic or photonic circuitry 214 in the second compartment 206. The sensor device 200 may further comprise an inlet opening 220 and an outlet opening 222 for controlling flow of the biological material into the first compartment 204.

The sensor device 200 may further comprise an internal wall 224 with a membrane area 226 defining through-going openings 228, the internal wall 224 separating the first sub-compartment 205*a* and the second sub-compartment 205*b*. The sensor device 200 may further comprise a protective coating 230 on the membrane area 226 and a protein filter 232 on or below the membrane area 226.

In contrast to the sensor device 100 of the first embodiment, the sensor device 200 of the second embodiment 200 comprises at least one sensor receptor element 210 and at least one sensor transducer element 216 configured to communicate wirelessly through the barrier 208. For instance, the at least one sensor transducer element 216 may be configured to transmit an interrogation electromagnetic signal through the barrier 208 to the at least one sensor receptor element 210 and to receive a response signal from the at least one sensor receptor element 210 for reading out a signal from the at least one sensor receptor element 210.

The communication between the at least one sensor transducer element 216 and the at least one sensor receptor element 210 may be performed via a light signal. The substrate 212 may be configured to carry a photonic integrated circuit providing processing and/or transport of optical signals from the at least one sensor transducer element 216. However, even when the communication between the at least one sensor transducer element 216 and the at least one sensor receptor element 210 is performed via light signals, the at least one sensor transducer element 216 may still output an electrical signal and may be arranged in an electronic circuitry.

The at least one sensor transducer element 216 may comprise a light emitting diode (LED) or any other light source for generating the light signal forming the interrogation signal. The at least one sensor transducer element 216 may further comprise a photodetector for detecting the response signal from the at least one sensor receptor element 210.

The interrogation electromagnetic signal may alternatively use another frequency, which is not optical, so as to enable communicating for example through capacitive or inductive communication. For instance, the communication between the at least one sensor transducer element 216 and the at least one sensor receptor element 210 may then use a signal frequency in a range of 10 mHz-1 GHz. The at least one sensor transducer element 216 may thus receive a response signal representative of an electrical property of the at least one sensor receptor element 210, such as a response signal representative of a potential, charge, or impedance of the at least one sensor receptor element 210.

The at least one sensor receptor element 210 may comprise materials deposited in a desired location at the first surface of the barrier 208 for selective interaction with specific target analytes. For instance, the at least one sensor receptor element 210 may comprise ion selective membranes, ion exchange membranes, ionophores, enzymes, antibodies, nanobodies, DNA, aptamers, molecularly imprinted polymers, organelles, cells, or optically active materials, such as fluorophores, phosphors, electrochemiluminescent or photoelectrochemical materials, or surface plasmon metal films.

The substrate 212 carrying electronic or photonic circuitry 214 may be arranged in contact with the second surface of the barrier 208 and may be attached to the second surface of the barrier 208, e.g., using an optical grade epoxy. Thus, the arrangement of the substrate 212 in relation to the barrier 208 may be configured to facilitate optical communication through the barrier 208.

It should be realized that communication between the at least one sensor transducer element 216 and the at least one sensor receptor element 210 using an interrogation electromagnetic signal may be used in other embodiments with different arrangements of the biocompatible enclosure. Thus, although the following third, fourth, fifth and sixth embodiments of the sensor device illustrate use of conducting material through the barrier for communicating between the at least one sensor transducer element and the at least one sensor receptor element, it should be realized that communication using interrogation electromagnetic signals may be used instead.

It should be further realized that at least one sensor receptor element 110 conductively connected to a transducer 116 as described in the first embodiment above may be combined with at least one further sensor receptor element 210 electromagnetically interrogated by a further transducer element 216, and that such combination may be provided in a single sensor device.

Figure 3:
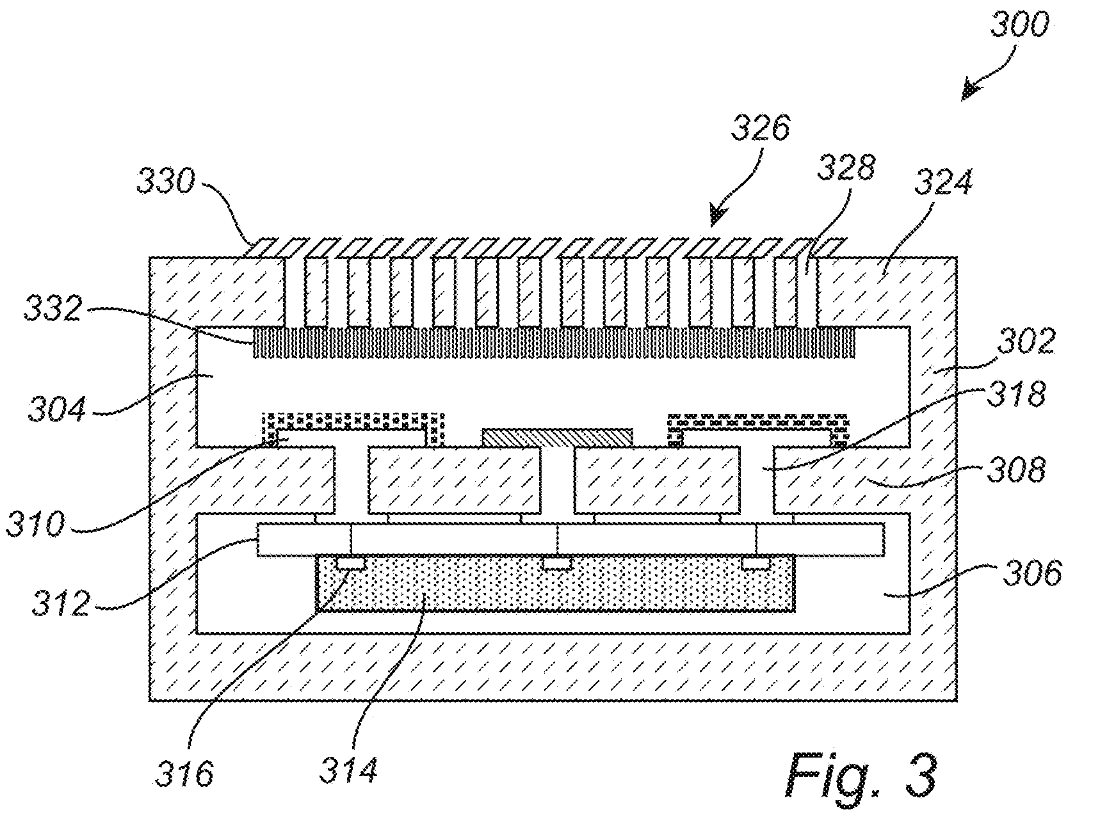
FIG. 3 is a schematic view of a cross-section of a sensor device according to a third embodiment.

Referring now to FIG. 3, a sensor device 300 according to a third embodiment will be described.

The sensor device 300 has many features in common with the sensor devices of the first and second embodiments. Only the features differing from these embodiments will be discussed in detail.

Thus, the sensor device 300 may comprise a biocompatible enclosure 302 defining a first compartment 304 and a second compartment 306. The sensor device 300 may comprise a substrate 312 carrying an electronic or photonic circuitry 314 in the second compartment 306.

The sensor device 300 may further comprise at least one sensor receptor element 310 arranged at a first surface of a barrier 308. The electronic or photonic circuitry 314 may further comprise at least one sensor transducer element 316 configured to communicate with the at least one sensor receptor element 310 through the barrier 308.

The at least one sensor transducer element 316 may be configured to communicate with the at least one sensor receptor element 310 through an electrical contact between the at least one sensor transducer element 316 and the at least one sensor receptor element 310. The barrier 308 may in this regard comprise through-going holes filled by a conducting material 318.

The first compartment 304 of the sensor device 300 is not separated into two sub-compartments. Rather, the first compartment 304 comprises a wall 324 defining an outer surface of the sensor device 300. The wall 324 comprises a membrane area 326 defining through-going openings 328. The sensor device 300 may further comprise a protective coating 330 on the membrane area 326 and a protein filter 332 on or below the membrane area 326. It should however be realized that the membrane area 326 may be used without the protective coating 330 and/or the protein filter 332.

Thus, the wall 324 comprising a membrane area 326 may define an external surface of the sensor device 300 through which a flow of the biological material may be provided into the first compartment 304. The through-going openings 328 of the membrane area 326, possibly together with the protein filter 332, may therefore control flow of biological material into the first compartment 304.

The sensor device 300 according to the third embodiment may be suitable for use when the sensor device 300 is arranged in a fluid, such as when the sensor device 300 is to be implanted and arranged in contact with a body fluid or when the sensor device 300 is to be used in a bioreactor. Alternatively, on the external surface of the wall 324 microneedles may be positioned, to control flow of biological material into the first compartment 304. These microneedles allow the sensor device 300 to be used as a transdermal sensor that is wearable on the external skin, for measurement of body fluids collected and transported by the microneedles through the skin.

Figure 4:
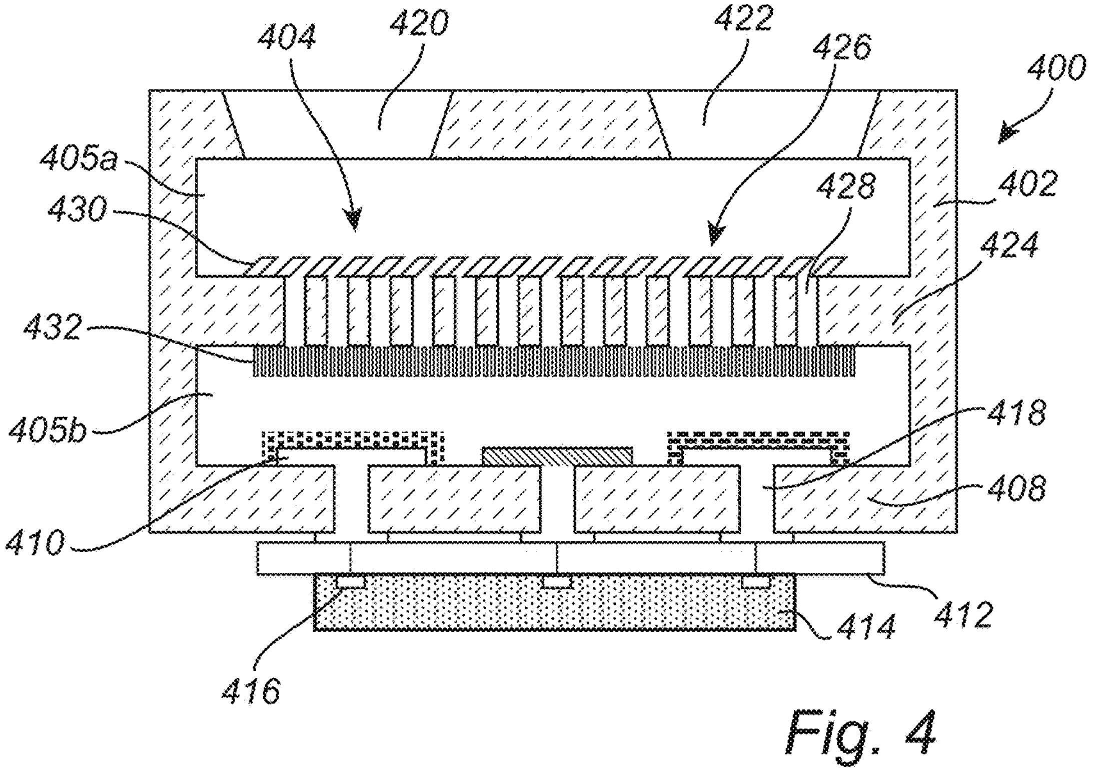
FIG. 4 is a schematic view of a cross-section of a sensor device according to a fourth embodiment.

Referring now to FIG. 4, a sensor device 400 according to a fourth embodiment will be described.

The sensor device 400 has many features in common with the sensor devices of the first, second, and third embodiments. Only the features differing from these embodiments will be discussed in detail.

Thus, the sensor device 400 may comprise a biocompatible enclosure 402 defining a first compartment 404, with a first sub-compartment 405*a* and a second sub-compartment 405*b*. The sensor device 400 may further comprise an inlet opening 420 and an outlet opening 422 for controlling flow of the biological material into the first compartment 404.

The sensor device 400 may further comprise an internal wall 424 with a membrane area 426 defining through-going openings 428, the internal wall 424 separating the first sub-compartment 405*a* and the second sub-compartment 405*b*. The sensor device 400 may further comprise a protective coating 430 on the membrane area 426 and a protein filter 432 on or below the membrane area 426.

The sensor device 400 may further comprise at least one sensor receptor element 410 arranged at a first surface of a barrier 408. The electronic or photonic circuitry 414 may further comprise at least one sensor transducer element 416 configured to communicate with the at least one sensor receptor element 410 through the barrier 408.

The at least one sensor transducer element 416 may be configured to communicate with the at least one sensor receptor element 410 through an electrical contact between the at least one sensor transducer element 416 and the at least one sensor receptor element 410. The barrier 408 may in this regard comprise through-going holes filled by a conducting material 418.

The sensor device 400 may comprise a substrate 412 carrying an electronic or photonic circuitry 414, which comprises the at least one sensor transducer element 416. In contrast to the first, second, and third embodiments, the substrate 412 is not arranged in a compartment of the biocompatible enclosure 402. Therefore, the barrier 408 forms an exterior surface of the biocompatible enclosure 402.

The sensor device 400 may be used in an application wherein the substrate 412 will not be exposed to biological material. For instance, the sensor device 400 may be used when the sensor device 400 is arranged externally to a human or animal body, or at least the substrate 412 is arranged externally to the human or animal body. Further, the flow of biological material may be well-controlled into the first compartment 404. For instance, that the flow of biological material may be transported through channels or conduits into and out of the first compartment 404 such that it may be ensured that the substrate 412 is not exposed to the flow of biological material.

Since the substrate 412 is not arranged in a hermetically sealed compartment, the electronic or photonic circuitry 414 may be more easily connected or connectable to external devices. For instance, the electronic or photonic circuitry 414 may be physically connected to an external device, e.g., through a wire, so as to allow wired communication between the electronic or photonic circuitry 414 and the external device.

Figure 5:
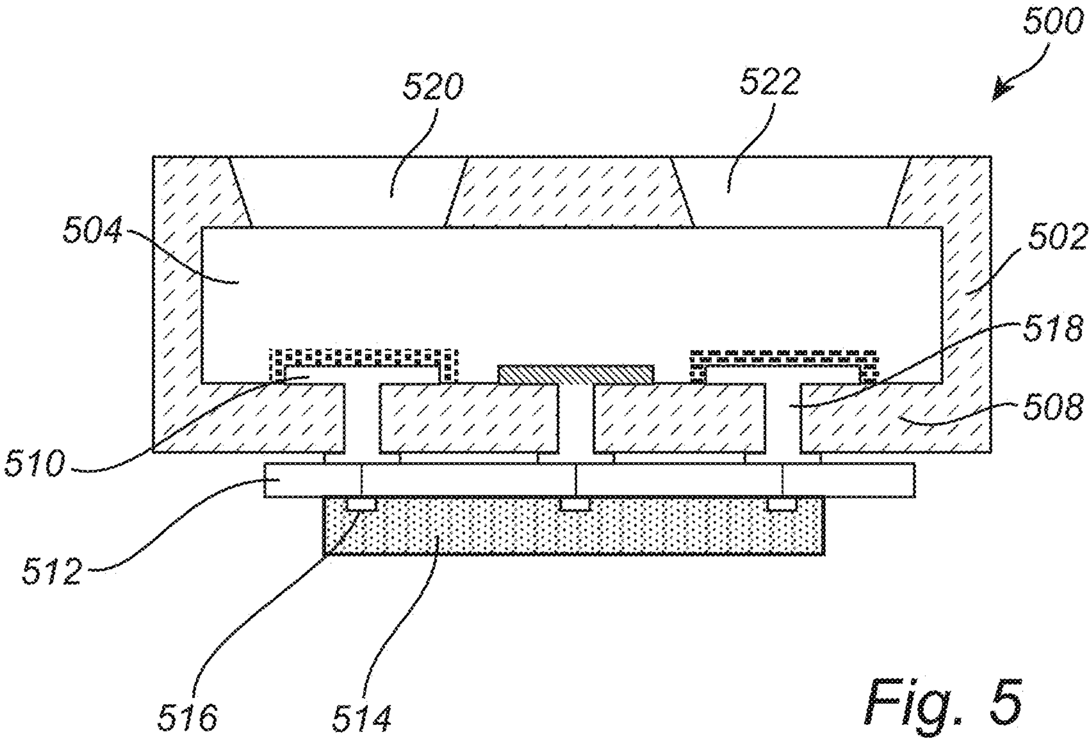
FIG. 5 is a schematic view of a cross-section of a sensor device according to a fifth embodiment.

Referring now to FIG. 5, a sensor device 500 according to a fifth embodiment will be described.

The sensor device 500 has features in common with the sensor devices of the first, second, third, and fourth embodiments. Only the features differing from these embodiments will be discussed in detail.

Thus, the sensor device 500 may comprise a biocompatible enclosure 502 defining a first compartment 504. The sensor device 500 may further comprise an inlet opening 520 and an outlet opening 522 for controlling flow of the biological material into the first compartment 504.

The sensor device 500 does not include any internal wall of the first compartment 504. Further, the sensor device 500 does not include any membrane area or protein filter for controlling particles or substances that are allowed to enter the compartment 504 in which the at least one sensor receptor element 510 is arranged. It should be realized that in some applications, no filtering of the biological material is needed.

The sensor device 500 may further comprise at least one sensor receptor element 510 arranged at a first surface of a barrier 508. The electronic or photonic circuitry 514 may further comprise at least one sensor transducer element 516 configured to communicate with the at least one sensor receptor element 510 through the barrier 508.

The at least one sensor transducer element 516 may be configured to communicate with the at least one sensor receptor element 510 through an electrical contact between the at least one sensor transducer element 516 and the at least one sensor receptor element 510. The barrier 508 may in this regard comprise through-going holes filled by a conducting material 518.

The sensor device 500 may comprise a substrate 512 carrying an electronic or photonic circuitry 514, which comprises the at least one sensor transducer element 516. Similar to the fourth embodiment, the substrate 512 is illustrated as not being arranged in a compartment of the biocompatible enclosure 502. Therefore, the barrier 508 forms an exterior surface of the biocompatible enclosure 502. However, it should be realized that the sensor device 500 which does not have any filtering of the flow of biological material may comprise a hermetically sealed second compartment in which the substrate 512 is arranged.

Figure 6:
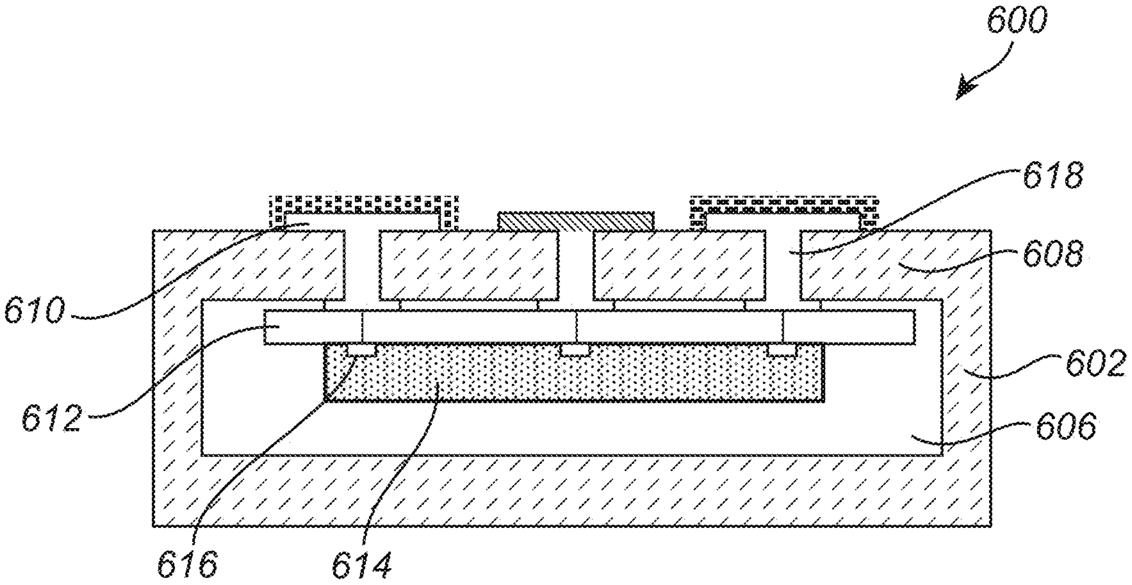
FIG. 6 is a schematic view of a cross-section of a sensor device according to a sixth embodiment.

Referring now to FIG. 6, a sensor device 600 according to a sixth embodiment will be described.

The sensor device 600 has features in common with the sensor devices of the first, second, third, fourth, and fifth embodiments. Only the features differing from these embodiments will be discussed in detail.

The sensor device 600 comprises a biocompatible enclosure 602 forming a compartment 606. The sensor device 600 further comprises a substrate 612 carrying an electronic or photonic circuitry 614 in the compartment 606.

The sensor device 600 may further comprise at least one sensor receptor element 610 arranged at a first surface of a barrier 608. The electronic or photonic circuitry 614 may further comprise at least one sensor transducer element 616 configured to communicate with the at least one sensor receptor element 610 through the barrier 608.

The at least one sensor transducer element 616 may be configured to communicate with the at least one sensor receptor element 610 through an electrical contact between the at least one sensor transducer element 616 and the at least one sensor receptor element 610. The barrier 608 may in this regard comprise through-going holes filled by a conducting material 618.

The sensor device 600 comprises the substrate 612 arranged in a hermetically sealed compartment 606. Thus, the substrate 612 with the electronic or photonic circuitry 614 is protected from making contact with biological material. The sensor device 600 is therefore suited for being arranged in an environment comprising biological material, such as being implanted in the human or animal body or being arranged in a bioreactor.

The at least one sensor receptor element 610 is not arranged in any compartment of the sensor device 600. Thus, the sensor device 600 does not provide any control of flow of biological material and the at least one sensor receptor element 610 is exposed at the first surface of the barrier 608.

The sensor device 600 may be useful when there is no need for controlling flow of biological material that is to be sensed by the at least one sensor receptor element 610 but there is still a need to protect the electronic or photonic circuitry 614 comprising the at least one sensor transducer element 616 from making contact with the biological material.

Figure 7:
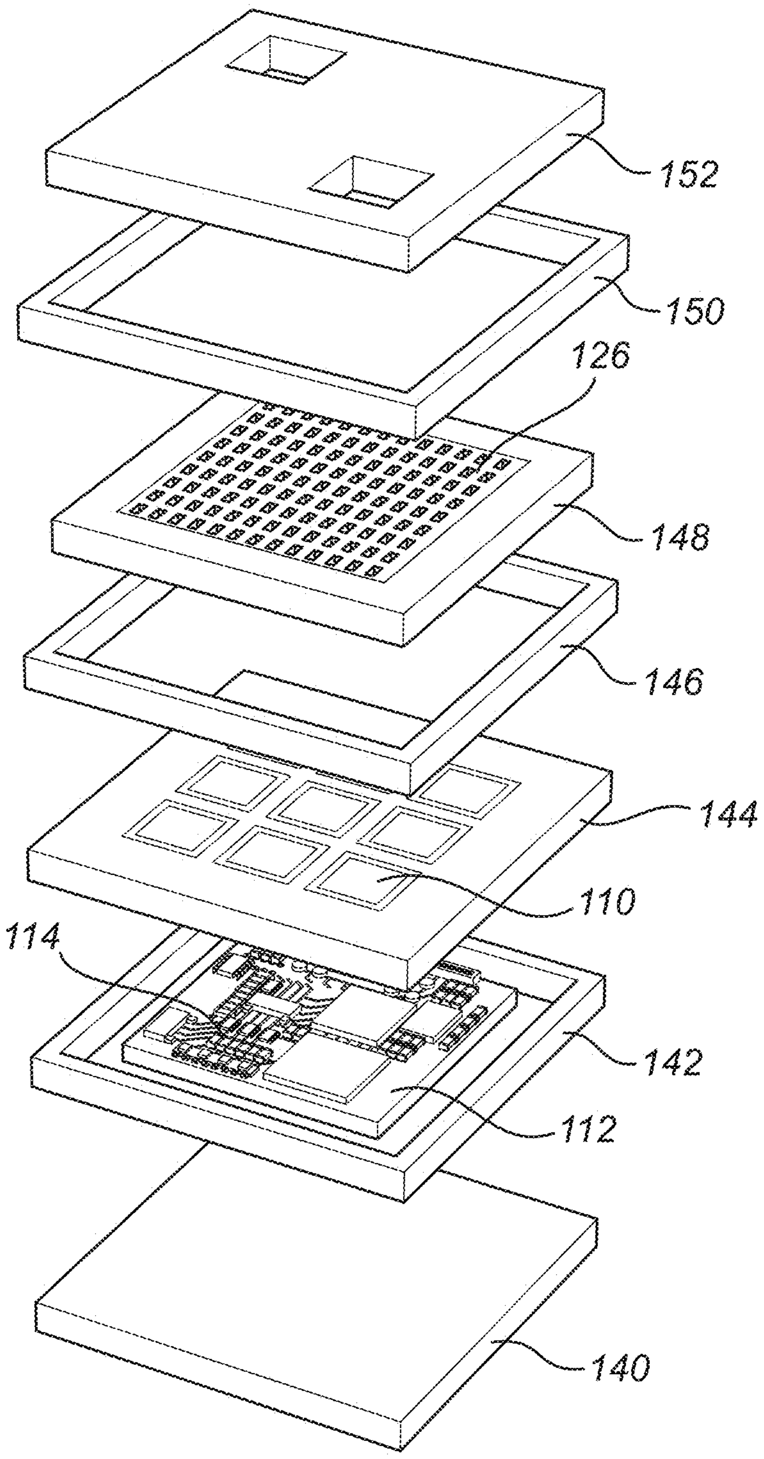
FIG. 7 is a schematic view illustrating forming of the sensor device of the first embodiment using stacking of plates.

Referring now to FIG. 7, the use of stacked plates for forming the sensor device 100 will be discussed in more detail. It should however be realized that any of the sensor device according to the first, second, third, fourth, fifth, or sixth embodiments may be formed using stacked plates.

As shown in FIG. 7, a plurality of plates 140, 142, 144, 146, 148, 150, and 152 may be used for forming the sensor device 100. Each plate may define a layer in the sensor device 100. The different plates may be separately manufactured, such that each plate is first manufactured individually before the plates are assembled for forming a finalized sensor device 100.

This implies that the manufacturing of each individual plate need only take into account requirements for the specific manufacturing of the plate and need not be limited to materials or properties (temperature, etc.) according to requirements for manufacturing of other plates.

The forming of the sensor device 100 includes a bottom plate 140 formed from a biocompatible material, wherein the bottom plate 140 will define a bottom of the second compartment 106. The bottom plate 140 may be formed by a homogeneous plate of biocompatible material, for instance glass.

The forming of the sensor device 100 further includes a first spacer plate 142. The first spacer plate 142 defines edges of the sensor device 100 and defines a spacing between the edges, in which the substrate 112 carrying the electronic or photonic circuitry 114 may be arranged. The first spacer plate 142 may be formed from a biocompatible material.

The forming of the sensor device 100 further includes a barrier plate 144. The barrier plate 144 defines the barrier 108 which separates the at least sensor receptor element 110 from the at least one sensor transducer element 116. The barrier plate 144 may be formed from a biocompatible material.

When the sensor receptor element 110 and the at least one sensor transducer element 116 are configured to communicate through electrical contact, through-going holes may first be etched through the barrier plate 144 and these through-going holes may then be filled by conducting material 118 (e.g., copper). Alternatively, the barrier plate 144 is produced by filling the space between conductive cylinders forming the conducting material 118 (e.g., tungsten) with hot molten glass and subsequently solidified. Thereafter, metals for forming the at least one sensor receptor element 110 in the form of electrodes may be deposited on the barrier plate 144. The metals may include materials that are not compatible with CMOS processing, such as carbon, gold, silver, and platinum.

The first spacer plate 142 may comprise structures onto which the substrate 112 may be mounted such that the first spacer plate 142 may carry the substrate 112 when the sensor device 100 is to be mounted. However, according to an alternative, the substrate 112 may be mounted to the bottom plate 140 or to the barrier plate 144 before or after the first spacer plate 142 is arranged around the substrate 112.

The substrate 112 may be manufactured individually, for example by semiconductor processing, such as CMOS processing, or flat panel display processing on glass, or printed circuit board processing. The electronic or photonic circuitry 114 may thus be formed before the substrate 112 is mounted for forming the sensor device 100.

The substrate 112 may be mounted by arranging the substrate 112 in contact with the second surface of the barrier 108. The substrate 112 may then be bonded, such as thermally bonded, to the barrier plate 144 using solder bumps, conductive epoxy, or ball grid arrays for also connecting the at least one transducer element 116 to the conducting material 118.

If the at least one sensor receptor element 110 and the at least one sensor transducer element 116 are to communicate through an interrogation electromagnetic signal, the substrate 112 may also be arranged in contact with the second surface of the barrier 108 and bonded to the barrier plate 144. The bonding of the substrate 112 to the barrier plate 144 may for instance be achieved using optical grade epoxy.

If the at least one sensor receptor element 110 is to be provided with materials for selective capturing of a target analyte, such materials may be deposited after the substrate 112 has been bonded to the second surface of the barrier 108. In such case, the materials may be deposited using low temperature processes (so as not to harm the substrate 112).

The forming of the sensor device 100 further includes a second spacer plate 146. The second spacer plate 146 defines edges of the sensor device 100 and defines a spacing between the edges defining the second sub-compartment **105*b*, in which the at least one sensor receptor element 110 may be arranged. The second spacer plate 146** may be formed from a biocompatible material.

The forming of the sensor device 100 further includes a membrane plate 148. The membrane plate 148 defines an internal wall 124 of the first compartment 104. Through-going openings 128 may be etched through the internal wall 124 for forming a membrane area 126. Further, a protective coating 130 may be provided on the membrane area 126. Also, a protein filter 132 may be provided above or below the membrane area 126. The membrane plate 148 may be formed from a biocompatible material through which the through-going openings 128 are defined.

The forming of the sensor device 100 further includes a third spacer plate 150. The third spacer plate 150 defines edges of the sensor device 100 and defines a spacing between the edges defining the first sub-compartment **105*a* into which a flow of biological material is received. The third spacer plate 150** may be formed from a biocompatible material.

The forming of the sensor device 100 further includes a top plate 152 formed from a biocompatible material, wherein the top plate 152 will define a top of the first compartment 104. The top plate 152 may be formed by a homogeneous plate of biocompatible material, for instance glass. Further, inlet openings 120 and outlet openings 122 may be defined through the top plate 152.

It should be realized that the plates may define structures of a plurality of sensor devices 100 such that the plates may be used for parallel manufacturing of a plurality of sensor devices 100 on wafer-level. Thus, the edges of the sensor device 100 may constitute interior walls within the plates.

The edges of the plates may be bonded to each other for forming of the assembled sensor device 100. The bonding of the edges may be done by laser welding. This may for instance be suitable if the plates are formed from glass.

Figure 8:
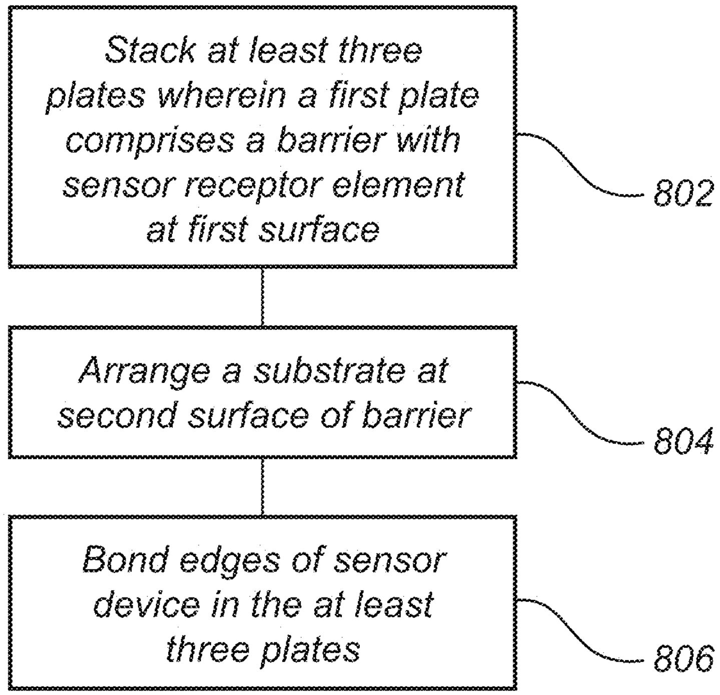
FIG. 8 is a flow chart of a method for manufacturing of a sensor device.

Referring now to FIG. 8, a method for manufacturing a sensor device will be further described.

The method comprises stacking 802 at least three plates. The three plates may each be formed of biocompatible material.

The at least three plates comprise a first plate comprising a barrier formed from biocompatible and electrically insulating material, wherein the barrier has a first surface and a second surface opposite to the first surface and wherein at least one sensor receptor element is arranged at the first surface of the barrier.

The method further comprises arranging 804 a substrate at the second surface of the barrier, wherein the substrate carries an electronic or photonic circuitry comprising at least one sensor transducer element for reading out signals from the at least one sensor receptor element by communication through the barrier.

The method further comprises bonding 806 edges of at least one sensor device in the at least three plates to each other so as to form a biocompatible enclosure defining at least one compartment, wherein the biocompatible enclosure comprises the barrier of the first plate and wherein the at least one compartment is configured to control transport of the biological material into the compartment or wherein the at least one compartment is configured to form a hermetical seal around the substrate carrying the electronic or photonic circuitry. The bonding of the edges may comprise laser welding of the edges for forming a bond.

The three plates may comprise a second plate forming a spacer. Thus, the compartment may be formed between the first plate and the third plate with the second plate defining side walls of the compartment.

When the at least one compartment is configured to control transport of the biological material into the compartment, the at least one sensor receptor element is arranged in the compartment. Thus, in such case, the second and third plates may be arranged in relation to the first surface of the first plate such that the at least one sensor receptor element will be arranged within the compartment.

When the at least one compartment is configured to form a hermetical seal around the substrate, the second and third plates may be arranged in relation to the second surface of the first plate such that the substrate will be arranged within the compartment.

It should be realized that two compartments may be formed by stacking further plates, such that the sensor device may be manufactured to both control transport of the biological material into a first compartment and to form a hermetical seal around the substrate in a second compartment.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A sensor device for sensing a property of a biological material, said sensor device comprising:

a biocompatible enclosure defining at least one compartment, the biocompatible enclosure comprising a barrier having a first surface and a second surface opposite to the first surface, wherein the barrier is formed from biocompatible and electrically insulating material;

at least one sensor receptor element arranged at the first surface of the barrier;

an electronic or photonic circuitry comprising at least one sensor transducer element for reading out signals from the at least one sensor receptor element, wherein the electronic or photonic circuitry is arranged at the second surface of the barrier and wherein the at least one sensor receptor element and the at least one sensor transducer element are configured to communicate through the barrier; and wherein the at least one compartment is configured to control transport of the biological material into the at least one compartment or wherein the at least one compartment is configured to form a hermetical seal around the electronic or photonic circuitry;

wherein the sensor device is configured to be arranged with the at least one sensor receptor element making contact with the biological material for sensing the property of the biological material and the electronic or photonic circuitry comprising the at least one sensor transducer element being protected from making contact with the biological material, wherein the barrier of the biocompatible enclosure is a first wall and wherein the sensor device further comprises a second wall formed from biocompatible material, wherein the second wall is arranged facing the first surface of the first wall and the second wall comprises a membrane area comprising a plurality of through-going openings through the second wall for selectively passing the biological material through the second wall.

2. The sensor device according to claim 1, further comprising a substrate carrying the electronic or photonic circuitry.

3. The sensor device according to claim 1, wherein the barrier of the biocompatible enclosure comprises through-going holes, wherein the through-going holes are filled by a conducting material for providing electrical contact between the at least one sensor receptor element and the at least one sensor transducer element.

4. The sensor device according to claim 1, wherein the at least one sensor transducer element is configured to transmit an interrogation electromagnetic signal through the barrier to the at least one sensor receptor element and for receiving a response signal from the at least one sensor receptor element.

5. The sensor device according to claim 1, further comprising a protective coating on the membrane area for protecting the through-going openings from being blocked.

6. The sensor device according to claim 1, further comprising a protein filter on or below the membrane area for selectively excluding protein access to the at least one sensor receptor element.

7. The sensor device according to claim 1, wherein the second wall is arranged as an internal wall within a compartment of the at least one compartment configured to control transport of the biological material into the compartment, wherein the second wall separates the compartment into two sub-compartments and is configured to provide fluid communication between the two sub-compartments through the membrane area.

8. The sensor device according to claim 1, wherein the at least one compartment comprises a first compartment configured to control flow of the biological material into the first compartment, wherein the biocompatible enclosure comprises an inlet opening for allowing flow of the biological material into the first compartment and an outlet opening for allowing flow of the biological material out of the first compartment.

9. The sensor device according to claim 8, wherein the at least one compartment further comprises a second compartment configured to form a hermetical seal around the electronic or photonic circuitry.

10. The sensor device according to claim 1, wherein the sensor device comprises a plurality of stacked plates forming a stack with the plurality of stacked plates bonded to each other at edges of the sensor device, wherein the plurality of stacked plates include at least a first plate carrying the at least one sensor receptor element, a second plate for defining a spacing, and a third plate, wherein the first plate, the second plate and the third plate are bonded together to form the biocompatible enclosure with the second plate defining a spacing between the first plate and the third plate.

11. The sensor device according to claim 1, wherein the at least one sensor receptor element comprises carbon, graphene, gold, silver, platinum and/or conductive polymer.

12. The sensor device according to claim 1, wherein the at least one sensor receptor element is configured to capture an analyte of interest.

13. The sensor device according to claim 1, wherein the sensor device is configured to be at least partly implantable in a human or animal body.

14. A method for manufacturing a sensor device for sensing a property of a biological material, said method comprising:

stacking at least three plates, each formed of biocompatible material, wherein a first plate of the at least three plates comprises a barrier formed from biocompatible and electrically insulating material, wherein the barrier has a first surface and a second surface opposite to the first surface and wherein at least one sensor receptor element is arranged at the first surface of the barrier;

arranging at least one sensor receptor element at the first surface of the barrier;

arranging an electronic or photonic circuitry at the second surface of the barrier, wherein the electronic or photonic circuitry comprises at least one sensor transducer element for reading out signals from the at least one sensor receptor element by communication through the barrier, bonding edges of at least one sensor device in the at least three plates to each other so as to form a biocompatible enclosure defining at least one compartment, wherein the biocompatible enclosure comprises the barrier of the first plate and wherein the at least one compartment is configured to control transport of the biological material into the at least one compartment or wherein the at least one compartment is configured to form a hermetical seal around the electronic or photonic circuitry, wherein the sensor device is configured to be arranged with the at least one sensor receptor element making contact with the biological material for sensing the property of the biological material and the electronic or photonic circuitry comprising the at least one sensor transducer element being protected from making contact with the biological material, and wherein the barrier of the biocompatible enclosure is a first wall and wherein the sensor device further comprises a second wall formed from biocompatible material, wherein the second wall is arranged facing the first surface of the first wall and the second wall comprises a membrane area comprising a plurality of through-going openings through the second wall for selectively passing the biological material through the second wall.

15. The method according to claim 14, wherein said arranging an electronic or photonic circuitry comprises arranging a substrate at the second surface of the barrier, wherein the substrate carries the electronic or photonic circuitry.

16. The method according to claim 14, wherein bonding of the edges comprises laser welding the edges for forming a bond.

17. A sensor device for sensing a property of a biological material, said sensor device comprising:

a biocompatible enclosure defining at least one compartment, the biocompatible enclosure comprising a barrier having a first surface and a second surface opposite to the first surface, wherein the barrier is formed from biocompatible and electrically insulating material;

at least one sensor receptor element arranged at the first surface of the barrier;

an electronic or photonic circuitry comprising at least one sensor transducer element for reading out signals from the at least one sensor receptor element, wherein the electronic or photonic circuitry is arranged at the second surface of the barrier and wherein the at least one sensor receptor element and the at least one sensor transducer element are configured to communicate through the barrier; and wherein the at least one compartment is configured to control transport of the biological material into the at least one compartment or wherein the at least one compartment is configured to form a hermetical seal around the electronic or photonic circuitry;

wherein the sensor device is configured to be arranged with the at least one sensor receptor element making contact with the biological material for sensing the property of the biological material and the electronic or photonic circuitry comprising the at least one sensor transducer element being protected from making contact with the biological material, wherein the at least one compartment comprises a first compartment configured to control flow of the biological material into the first compartment, wherein the biocompatible enclosure comprises an inlet opening for allowing flow of the biological material into the first compartment and an outlet opening for allowing flow of the biological material out of the first compartment.

18. The sensor device according to claim 17, wherein the at least one compartment further comprises a second compartment configured to form a hermetical seal around the electronic or photonic circuitry.

* * * * *